United States Patent
Mahmood et al.

(10) Patent No.: US 9,594,032 B2
(45) Date of Patent: Mar. 14, 2017

(54) EXTENDED FIELD ITERATIVE RECONSTRUCTION TECHNIQUE (EFIRT) FOR CORRELATED NOISE REMOVAL

(71) Applicant: Okinawa Institute of Science and Technology School Corporation, Okinawa (JP)

(72) Inventors: Faisal Mahmood, Okinawa (JP); Lars-Göran Wallentin Öfverstedt, Okinawa (JP); Bo Ulf Skoglund, Okinawa (JP)

(73) Assignee: OKINAWA INSTITUTE OF SCIENCE AND TECHNOLOGY SCHOOL CORPORATION, Okinawa (JP)

( * ) Notice: Subject to any disclaimer, the term of this patent is extended or adjusted under 35 U.S.C. 154(b) by 0 days.

(21) Appl. No.: 14/770,245

(22) PCT Filed: Mar. 5, 2014

(86) PCT No.: PCT/JP2014/001214
§ 371 (c)(1),
(2) Date: Aug. 25, 2015

(87) PCT Pub. No.: WO2014/141630
PCT Pub. Date: Sep. 18, 2014

(65) Prior Publication Data
US 2016/0003752 A1 Jan. 7, 2016

Related U.S. Application Data

(60) Provisional application No. 61/779,116, filed on Mar. 13, 2013.

(51) Int. Cl.
*G06K 9/00* (2006.01)
*G01N 23/04* (2006.01)
*G06T 11/00* (2006.01)

(52) U.S. Cl.
CPC .......... *G01N 23/046* (2013.01); *G06T 11/006* (2013.01); *G01N 2223/401* (2013.01);
(Continued)

(58) Field of Classification Search
None
See application file for complete search history.

(56) References Cited

U.S. PATENT DOCUMENTS 5,848,114 A   12/1998  Kawai et al.
6,418,243 B1   7/2002  Skoglund et al.
(Continued)

FOREIGN PATENT DOCUMENTS

JP   9-253079 A    9/1997
JP   2000-507007 A  6/2000
(Continued)

OTHER PUBLICATIONS

International Search Report (ISR) issued in PCT/JP2014/001214 mailed in Apr. 2014.
(Continued)

*Primary Examiner* — Atiba O Fitzpatrick
(74) *Attorney, Agent, or Firm* — Chen Yoshimura LLP

(57) ABSTRACT

Computerized method and system for improving 3D reconstruction images involves applying the Extended Field Iterative Reconstruction Technique (EFIRT) to remove correlated noise, in addition to with COMET (constrained maximum relative entropy tomography) or other regularization techniques to eliminate uncorrelated noise, wherein the EFIRT is applied by performing a set of successive reconstructions on an extended field larger than a region of interest (ROI); and extracting and averaging the ROI from said set of successive reconstructions.

10 Claims, 12 Drawing Sheets

(52) U.S. Cl.
CPC ... *G01N 2223/419* (2013.01); *G01N 2223/42* (2013.01); *G01N 2223/612* (2013.01); *G06T 2211/432* (2013.01)

(56) References Cited

U.S. PATENT DOCUMENTS

| | | | |
|---|---|---|---|
| 2003/0160622 A1* | 8/2003 | Duensing | A61B 5/0507 324/691 |
| 2004/0137519 A1 | 7/2004 | Skoglund et al. | |
| 2006/0120579 A1 | 6/2006 | Skoglund et al. | |
| 2006/0261269 A1 | 11/2006 | Skoglund | |
| 2007/0161044 A1 | 7/2007 | Skoglund et al. | |
| 2009/0283676 A1* | 11/2009 | Skoglund | G01N 23/046 250/307 |
| 2010/0005130 A1 | 1/2010 | Oktem et al. | |
| 2010/0054565 A1 | 3/2010 | Quinto et al. | |
| 2010/0223036 A1 | 9/2010 | Oktem et al. | |
| 2013/0077847 A1* | 3/2013 | Hansis | G06T 11/006 382/131 |

FOREIGN PATENT DOCUMENTS

| | | |
|---|---|---|
| JP | 2004-530119 A | 9/2004 |
| JP | 2005-538344 A | 12/2005 |
| JP | 2006-517667 A | 7/2006 |
| WO | 97/33255 A1 | 9/1997 |
| WO | 02/071336 A1 | 9/2002 |
| WO | 2004/006189 A | 1/2004 |
| WO | 2004/068415 A1 | 8/2004 |
| WO | 2007/0094721 A1 | 8/2007 |
| WO | 2007/114772 A1 | 10/2007 |
| WO | 2008/041945 A1 | 4/2008 |
| WO | 2008/055953 A2 | 5/2008 |

OTHER PUBLICATIONS

Written Opinion (PCT/ISA/237) issued in PCT/JP2014/001214 mailed in Apr. 2014.
Baba, "Principle of electron tomography reconstruction", Microscopy, Mar. 31, 2004, vol. 39, No. 1, p. 4-10.
Palenstijn et al., "Performance improvements for iterative electron tomography reconstruction using graphics processing units (GPUs)", Journal of Structural Biology, Nov. 2001, vol. 176, No. 2, p. 250-253.
Norlen et al., "Molecular cryo-electron tomography of vitreous tissue sections: current challenges", Journal of Microscopy, vol. 235, Pt 3 2009, pp. 293-307.
European Search Report dated Nov. 22, 2016, in a counterpart European patent application No. 14764705.1.
Lars-Goran Ofverstedt et al., "Automated Correlation and Averaging of Three-Dimensional Reconstructions Obtained by Electron Tomography", Journal of Structural Biology, Dec. 1997 (Dec. 1997), vol. 120, No. 3, pp. 329-342 (Cited in the ESR above.).
Ulf Skoglund et al., "Maximum-Entropy Three-Dimensional Reconstruction with Deconvolution of the Contrast Transfer Function: A Test Application with Adenovirus", Journal of Structural Biology, Nov. 1996 (Nov. 1996), vol. 117, No. 3, pp. 173-188 (Cited in the ESR above.).
R. A. Crowther et al., "Three dimensional image reconstruction on an extended field—a fast, stable algorithm", Nature, Oct. 11, 1974 (Oct. 11, 1974), vol. 251, No. 5475, pp. 490-492 (Cited in the ESR above.).

* cited by examiner

EXTENDED FIELD ITERATIVE RECONSTRUCTION TECHNIQUE (EFIRT) FOR CORRELATED NOISE REMOVAL

TECHNICAL FIELD

The present invention relates to a computer implemented method and system for removing correlated noise by applying Extended Field Iterative Reconstruction Technique (EFIRT) in three-dimensional (3D) structure reconstructions.

BACKGROUND ART

Nowadays tomographic reconstruction has become a widely used technique for structure determinations in medical and biological applications. Macromolecules such as proteins and nucleic acids are important biological macromolecules, which possess important functional information within their structure. In addition, most biological macromolecules including proteins are flexible, with enhanced ability to interact with other molecules. As such, structure determination has important applications especially for purposes of understanding interactions between molecules, and thus, is of vital importance in drug development.

Many standard 3D structure determination techniques, such as x-ray crystallography, nuclear magnetic resonance (NMR) or single particle cryo-electron microscopyare, are based on averaging, which may cause losses of most information about the conformation or flexibility of the macromolecular structure. To overcome this problem, cryo-electron tomography (Cryo-ET) is introduced, which involves taking transmission electron microscope (TEM) images of a cryo-specimen at different tilt angles and reconstructing a 3D tomogram through aligning and back projecting the different images. Cryo-ET preserves the native structure of molecules due to rapid freezing to liquid nitrogen temperature, and does not necessarily involve averaging. As a result, it enables a thorough study of flexible multi-domain proteins in the native state.

Cryo-ET 3D reconstructions of macromolecules encounter several types of noise. One type of noise is specimen noise, which is mainly due to rearrangement of the specimen during data recording or degradation due to electron beam damage. This type of noise is normally minimized using a sufficiently low dose. The low dose, however, increases the uncorrelated shot noise caused by low illumination. In addition, correlated noise can appear due to imperfections of the TEM detector. This is because, normally, a gain reference is created to equalize the responses from individual detector elements, but errors in the gain reference can give rise to noise that is correlated with a region of the detector rather than with the specimen.

Most uncorrelated shot noise in cryo-ET reconstructions can be significantly reduced using procedures for regularized refinement, such as constrained maximum entropy tomography (COMET). In medical applications the shot noise is generally avoided to a large extent since a high dose could be used. However, correlated noise emanating from the detector measurement is difficult to handle since this kind of noise is related to sensitivity variations across the detector surface. To ensure homogenous signal responses, flat-fielding is often used in practice, but given the variations in the quality of flat-fielding, the resulting base-line comes with variations. The variations around the base-line result in a position-correlated noise, which, in a 2D or 3D reconstruction, causes an increased background in a position dependent on the length of the direction orthogonal to the detector surface, or for many projections, in the untilted beam direction.

In light of the above, there is a need for improved techniques to remove correlated noise for enhanced three-dimensional (3D) reconstruction images.

SUMMARY OF INVENTION

Technical Problem

Accordingly, the present invention is directed to a scheme that substantially obviates one or more of the above-discussed and other problems due to limitations and disadvantages of the related art.

An object of the present invention is to provide a computer implemented system and method for removing correlated noise in 3D reconstructions.

Solution to Problem

To achieve these and other advantages and in accordance with the purpose of the present invention, as embodied and broadly described, in one aspect, the present invention provides a computer implemented method for removing correlated noise by applying Extended Field Iterative Reconstruction Technique (EFIRT) in a three-dimensional (3D) reconstruction, wherein the method comprises performing a set of successive reconstructions on an extended field larger than a region of interest (ROI); and extracting and averaging the ROI from said set of successive reconstructions.

In one respect, the present invention provides a computer implemented method including the above-referenced features, wherein the set of reconstructions is performed by increasing volumes of each successive reconstruction.

In another respect, the present invention provides a computer implemented method including the above-referenced features, and further comprising removing uncorrelated noise in said 3D reconstruction.

In yet another respect, the present invention provides a computer implemented method including the above-referenced features, wherein the 3D reconstruction is implemented via a Cryo-Electron Tomography (Cryo-ET) application.

In one respect, the present invention also provides an apparatus for improving a three-dimensional (3D) reconstruction of a sample, said apparatus programmed to execute instructions including: removing uncorrelated noise in said 3D reconstruction with regularization; and removing correlated noise in said 3D reconstruction by applying an Extended Field Iterative Reconstruction Technique (EFIRT) procedure.

In another respect, the present invention provides an apparatus including the above-referenced features, wherein said EFIRT procedure comprises performing a set of successive reconstructions on an extended field larger than a region of interest (ROI); and extracting and averaging the ROI from said set of successive reconstructions.

Advantageous Effects of Invention

Additional or separate features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

It is to be understood that both the foregoing general description and the following detailed description are exemplary and explanatory, and are intended to provide further explanation of the invention as claimed.

DESCRIPTION OF EMBODIMENTS

Figure 1:
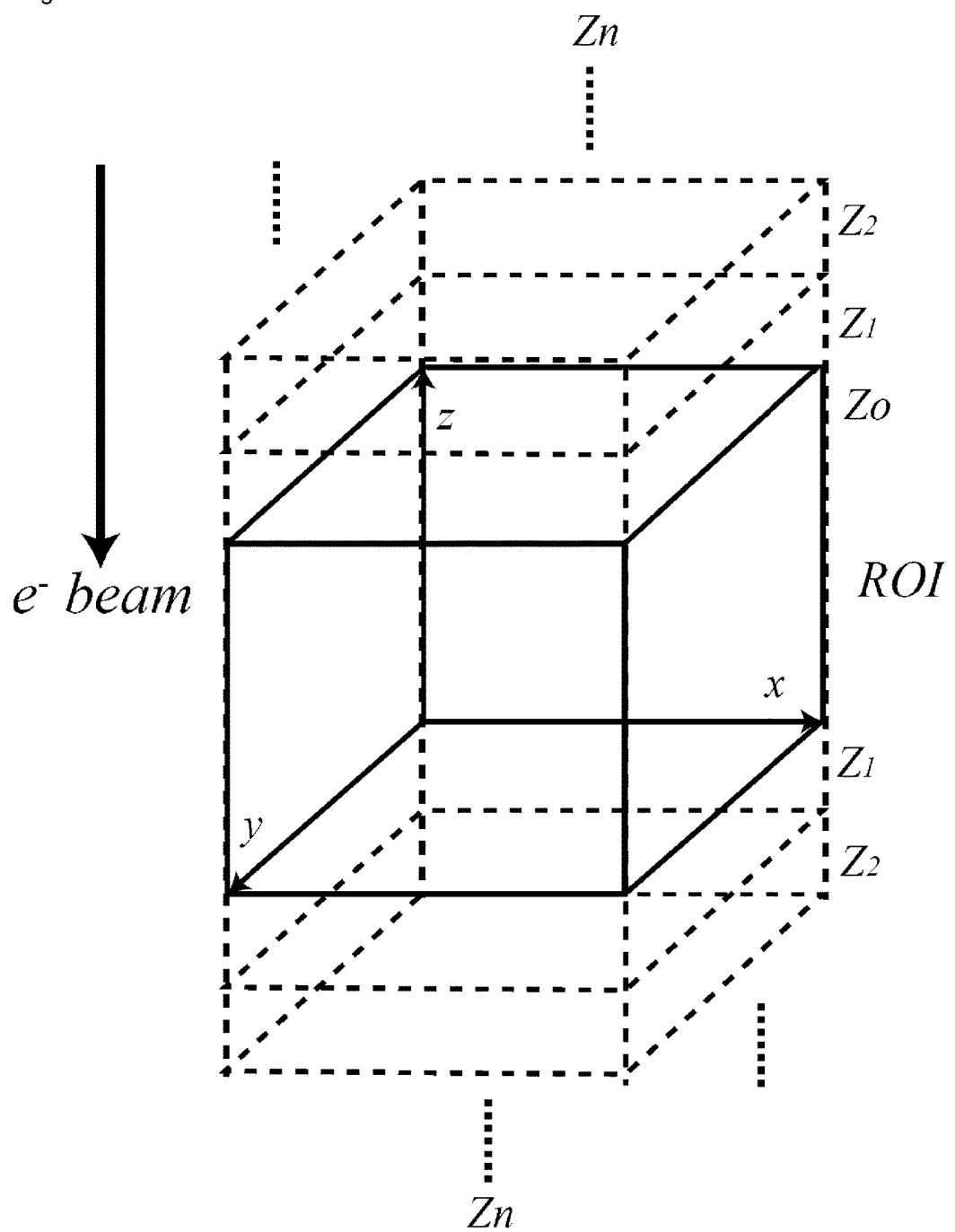
FIG. 1 is a diagram illustrating how to apply Extended Field Iterative Reconstruction Technique (EFIRT) in structure reconstructions according to an embodiment of the present invention, where only z is extended.

The present invention improves data processing in structure reconstructions, and more specifically, in some embodiments, provides a computer implemented method and system for removing correlated noise due to detector imperfection in 3D reconstructions.

In some embodiments of the present invention, the primary aspects of the system are the following.

Example 1

An algorithm for improving 3D reconstruction images comprises first removing the shot noise or uncorrelated noise with COMET or other regularization techniques, and furthermore, eliminating the residual noise, including correlated noise from detectors, by applying the EFIRT procedure. Notably, such algorithm can be implemented in data processing software, or a data processor or computer installed with said data processing software. Additionally, such algorithm can be applied in various applications including, without limitation to, Cryo-Electron Tomography (Cryo-ET) and other 3D reconstruction procedures/apparatus. It should be noted that in some embodiments, the removal of shot noise or uncorrelated noise prior to applying EFIRT to remove correlated noise can be accomplished in various ways, including, without limitation to, COMET. In other embodiments, the given data set may not contain significant shot noise, and so it is unnecessary to remove the shot noise before executing EFIRT to remove correlated noise. In other words, executing EFIRT to remove correlated noise can be a procedure independent of the removal of uncorrelated noise.

Example 2

An algorithm for removing correlated noise from detectors by EFIRT comprises performing a set of reconstructions on an extended field larger than the region of interest (ROI), followed by extracting and averaging the ROI from the set of reconstructions. In one embodiment, in performing the set of reconstructions, the volume of each successive reconstruction is increased. During extraction and averaging of the ROI, most correlated noise is either cut out or canceled.

Usually shot noise in Cryo-ET reconstructions can be significantly reduced using procedures for regularized refinement, such as constrained maximum entropy tomography (COMET), which essentially is an iterative algorithm for enhancing the contrast and resolution in cryo-ET by increasing the SNR. COMET can improve the fidelity of 3D reconstructions by filtering out most of the noise. Briefly speaking, COMET works in the following three steps:

Step 1

The density of the 3D reconstruction is modified in the iterations to increase (theoretically maximize) the entropy of the existing reconstruction. If the reconstructed normalized density is given by $$F(\vec{X})$$

and $$m(\vec{X})$$

is the prior or estimated probability distribution of the density, then the entropy function to be maximized can be given by the following equation:

$$S(F) = -\int F(\vec{X}) \ln\left(\frac{F(\vec{X})}{m(\vec{X})}\right) d^3\vec{X}$$

Step 2

Virtual projections are calculated from the reconstruction (i.e. the reconstruction from the previous iteration) in the direction of the tilts and a "goodness-of-fit" measure is determined. A good way to determine this measure is by using the statistical reduced chi-square function. As a general rule, a good fit is achieved with a reduced chi-square value of 1.0. Assuming that $$F_{calc}^{(i)}(\vec{X}^{(i)})$$

is the calculated density for the $i^{th}$ view/tilt and is the same for the observed, then the chi square function can be given by the following equation:

$$\chi^2_{(i)} = \frac{1}{N} \sum_{\overline{X}(i)} \frac{1}{\sigma^2_{(i)}(\overline{X}^{(i)})} \left[ b^{(i)} * F^{(i)}_{calc}(\overline{X}^{(i)}) - F^{(i)}_{obs}(\overline{X}^{(i)}) \right]^2$$

The goal is to iteratively reduce the chi-square fitting parameter $$\chi_{(i)}^2$$

so that it can be as close as possible to 1.0.

Step 3

An optimal balance between the maximization of entropy and minimization of chi-square function is determined and used to update the reconstruction before the next iteration.

COMET removes most of the shot noise from the reconstructions but correlated noise (usually from the detector) is still present. EFIRT is a technique to remove correlated noise by performing several reconstructions on an extended field, which is generally larger than the region of interest (ROI), and then averaging out the ROI from these reconstructions. The extended field basically provides a "rubbish" bin for most of the noise as extending the field dilutes the noise in a specific reconstruction. The extra region of the reconstruction outside the ROI enables the noise to spread out over a larger region, which leads to less and less noise in the ROI. By averaging, the dilution effect on true signals within the ROI is compensated while the noise is reduced.

The execution of EFIRT in structure reconstructions can be explained with reference to FIG. 1. Consider the z-axis in FIG. 1 to be the vertical axis, i.e., the direction of the electron field, and let $Z_o$ be the size of z for which the 3D reconstruction is desired. Reconstruction is performed for several increasing values of z such that $Z_1 < Z_2 < Z_3 < \ldots < Z_n$ resulting in 'n' number of 3D reconstructions. As shown in FIG. 1, each successive reconstruction has an increased volume in the direction of z.

The ROI with $z = Z_o$, which is the common region in all the reconstructions, is extracted from each reconstruction and averaged to give the effective reconstruction. Assuming that a single 3D reconstruction with $z = Z_n$ is represented by $R_{z(n)}$ and the same reconstruction after extracting the ROI with $z = Z_o$ is represented by $R_{zo(n)}$, then EFIRT can be represented by the following equation.

$$R_{eff} = \frac{R_{zo(0)} + R_{zo(1)} + R_{zo(2)} + \ldots + R_{zo(N-1)}}{N} = \frac{\sum_{k=0}^{N-1} R_{zo(k)}}{N}$$

Figure 2:
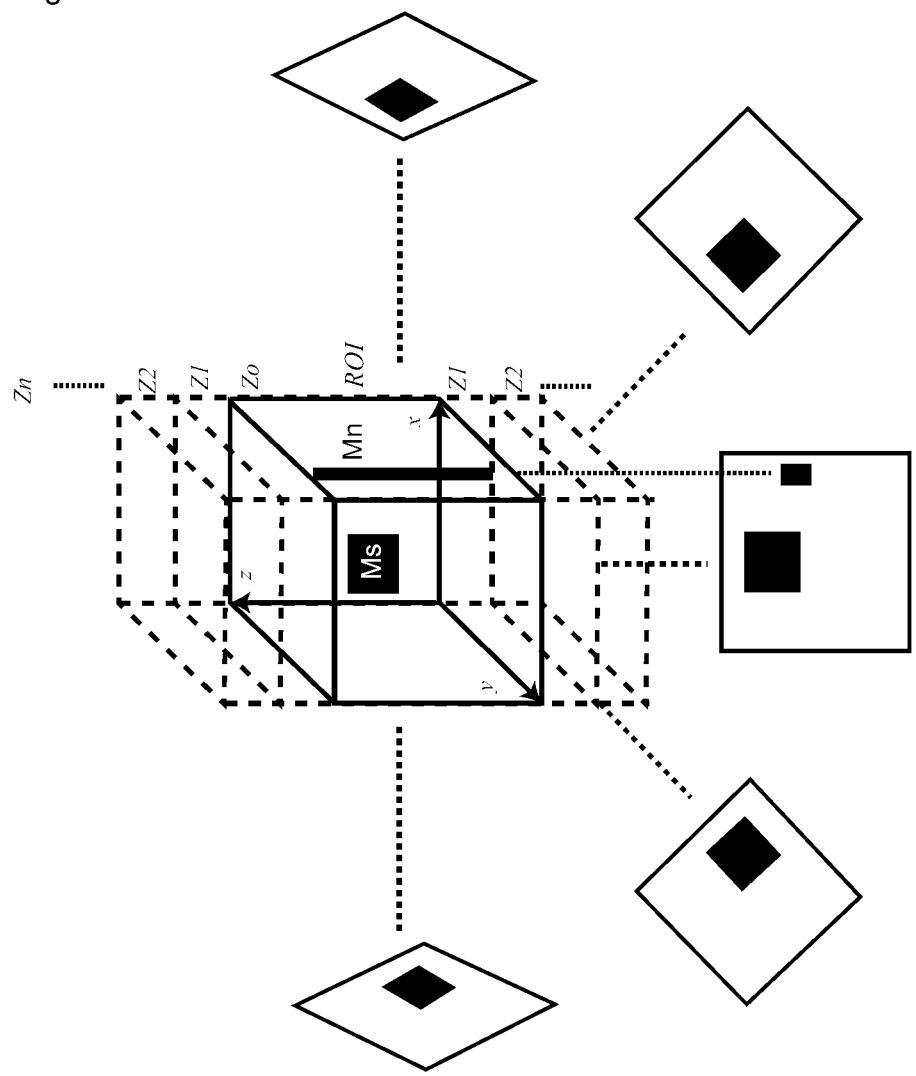
FIG. 2 is a diagram providing an alternative illustration how to apply EFIRT in structure reconstructions according to an embodiment of the present invention, where only z has been extended.

FIG. 2 demonstrates a 3D reconstruction from several 2D projections, which provides an alternative explanation of using the EFIRT procedure in removing correlated noise in 3D reconstructions. As seen in FIG. 2, the components of the 3D structure need to be present in all 2D projections so that it can be limited enough to form a rigid structure. However, noise does not have a representation in all 2D projections, and as a result, an unlimited structure can be formed, as shown in FIG. 2. When the same reconstruction is done on an extended field by increasing z, the rigid structure would remain, while the correlated noise would be distributed over a larger volume and thus would have decreased presence in the ROI.

The net mass inside the ROI is both from the density of the signal and from that of the noise. As shown in FIG. 2, Ms represents the mass of signal and Mn is the mass of noise. Assuming that $$\rho_{noise(1)}$$

is the noise associated density with the first reconstruction, N is the total number of reconstructions and k is the factor by which the volume is increased in each reconstruction by increasing z, then the net noise density of the final averaged reconstruction $$\rho_{net\ noise}$$

is given by the following equation:

$$\rho_{net\ noise} = \frac{\rho_{noise(1)}}{N} + \frac{\rho_{noise(1)}}{kN} \left( 1 + \frac{1}{2} + \frac{1}{3} + \ldots + \frac{1}{(N-1)} \right)$$

Based on this equation, the first term will decrease because N is in the denominator. The second term has a harmonic series, which is a divergent series, but it also has two terms in the denominator k and N, the product of which will always be larger than the harmonic series, thereby decreasing the overall factor. As such, the overall density of noise will decrease by using EFIRT in 3D reconstructions.

FIGS. 3-7 illustrate an example using EFIRT for 3D reconstructions according to an embodiment of the present invention. In this example, EFIRT is applied to the reconstruction of a protein receptor specimen, the glucocorticoid receptor (GR), from a low-dose Cryo-ET tilt series. Ten reconstructions were performed with the dimensions 250× 250×250 to 250×250×700 with z having an incremental increase of 50 grid points. The common region 250×250× 250 was cut out from all reconstructions and the average was calculated.

Figure 3:
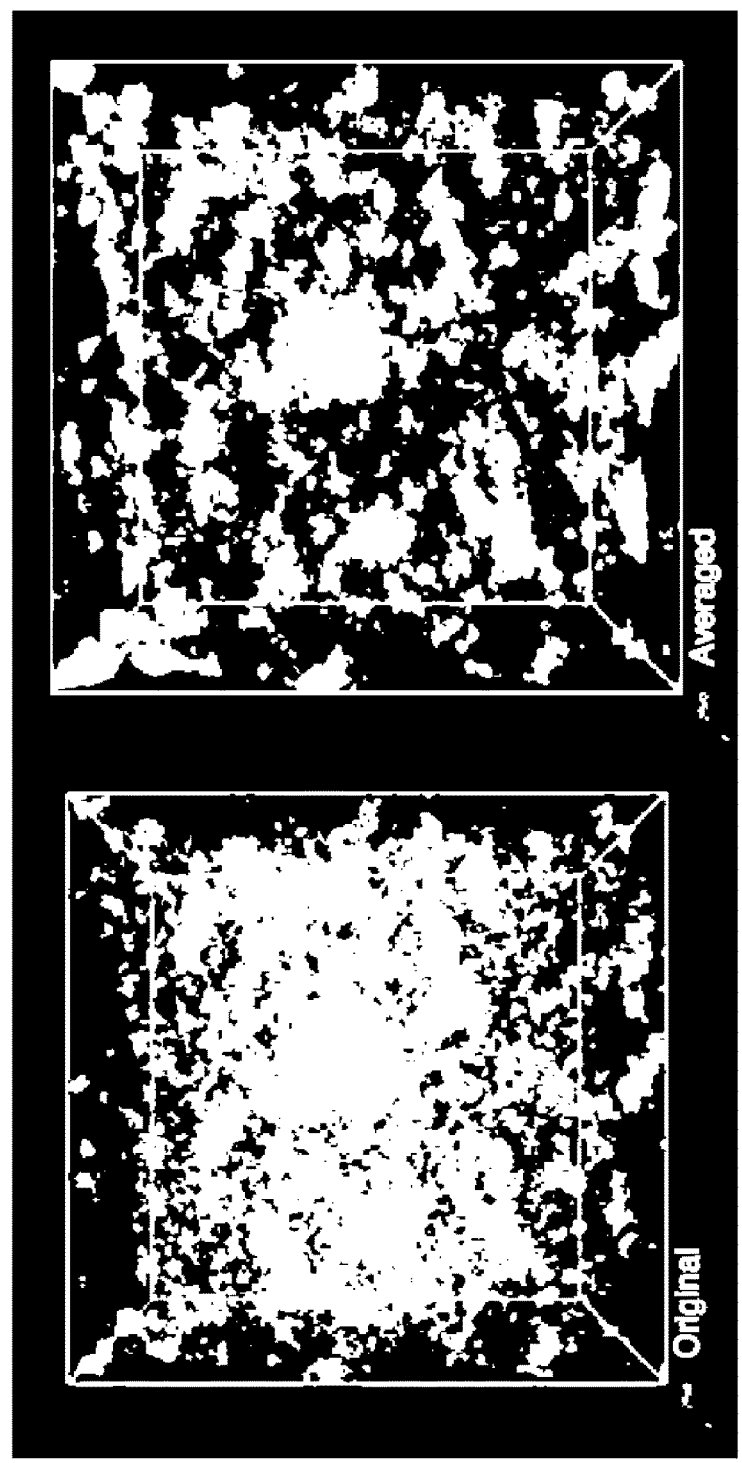
FIG. 3 illustrates an example using EFIRT for 3D reconstructions according to an embodiment of the present invention.

FIG. 3 shows volume renderings of the initial and final averaged EFIRT reconstructions. As seen in FIG. 3, the 3D reconstruction of this GR sample with EFIRT presents a higher image quality with less noise, as compared to the 3D reconstruction without EFIRT.

Figure 4:
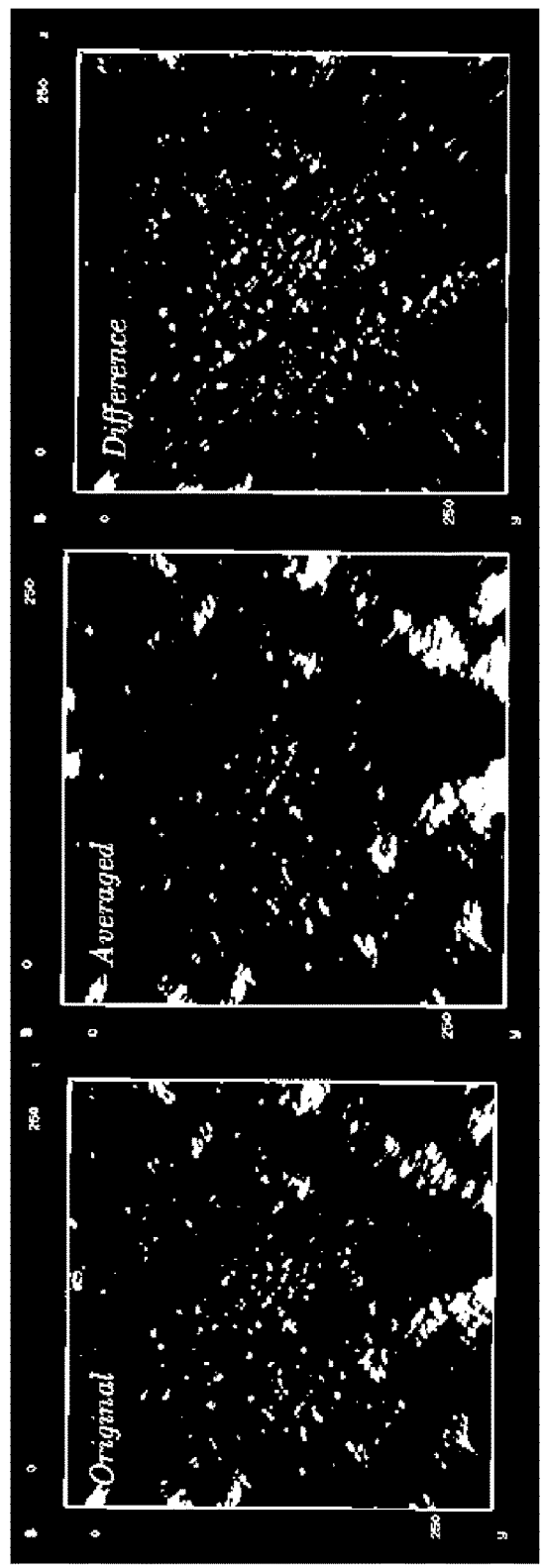
FIG. 4 illustrates an example using EFIRT for 3D reconstructions according to an embodiment of the present invention.

To further visualize the effect of EFIRT, FIG. 4 shows thin slices of both the original and EFIRT averaged reconstructions and the difference between them. Clearly, the EFIRT-applied and averaged reconstruction is less noisy and has an enforced signal with higher SNR, as compared to the original reconstruction. The difference shows the amount of noise being removed.

Figure 5:
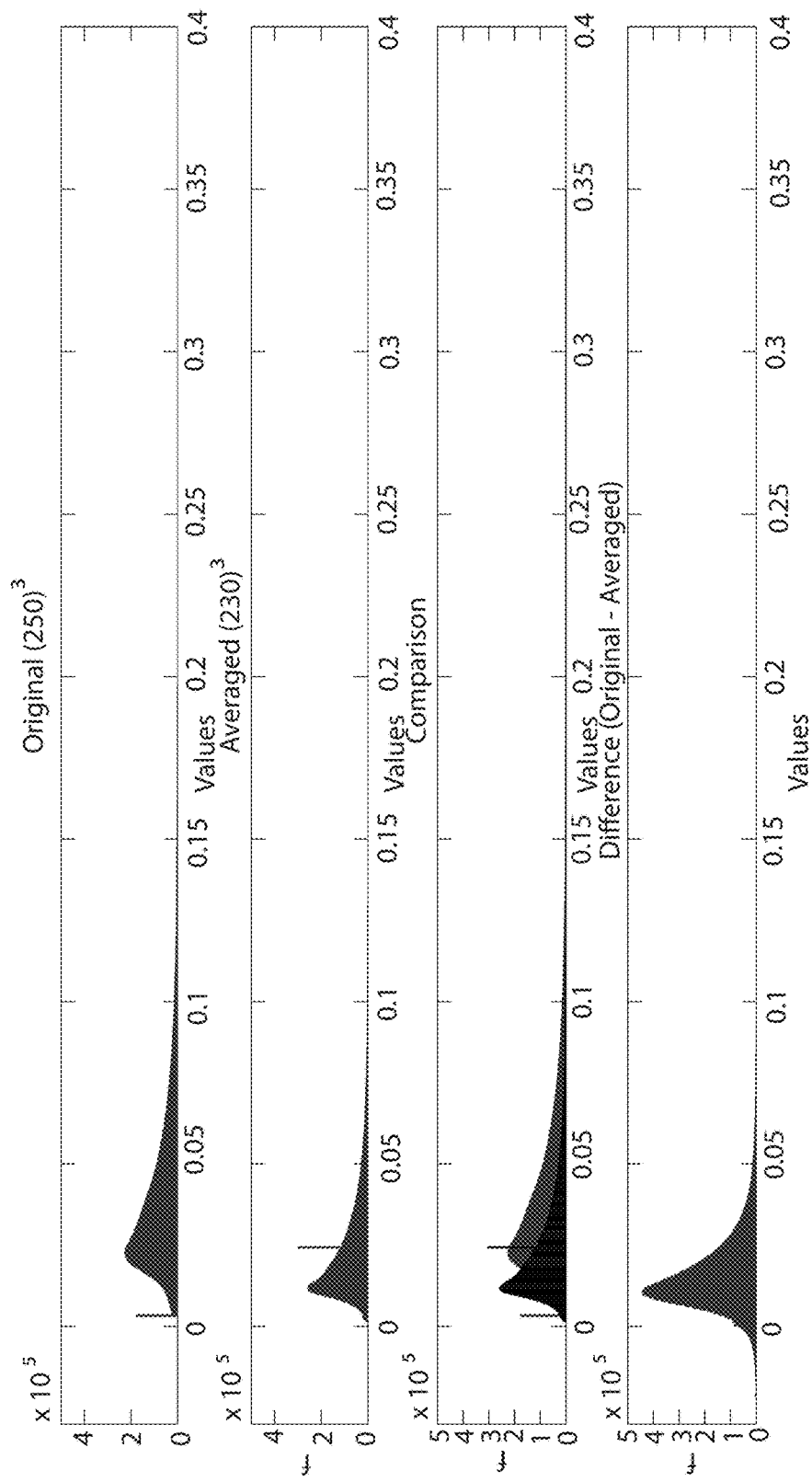
FIG. 5 illustrates an example using EFIRT for 3D reconstructions according to an embodiment of the present invention.

The effect of EFIRT is further illustrated in FIG. 5, which presents the histograms of the original and EFIRT averaged reconstructions and their comparison and difference. As compared to the original histogram, it is clear that the averaged histogram has lower values, thus having a shift towards the left and a higher peak. In the averaged and original histograms, the straight line of values in the beginning is a result of COMET, which converts all negative values to positive. Again, the difference histogram shows the amount of noise being removed.

Figure 6:
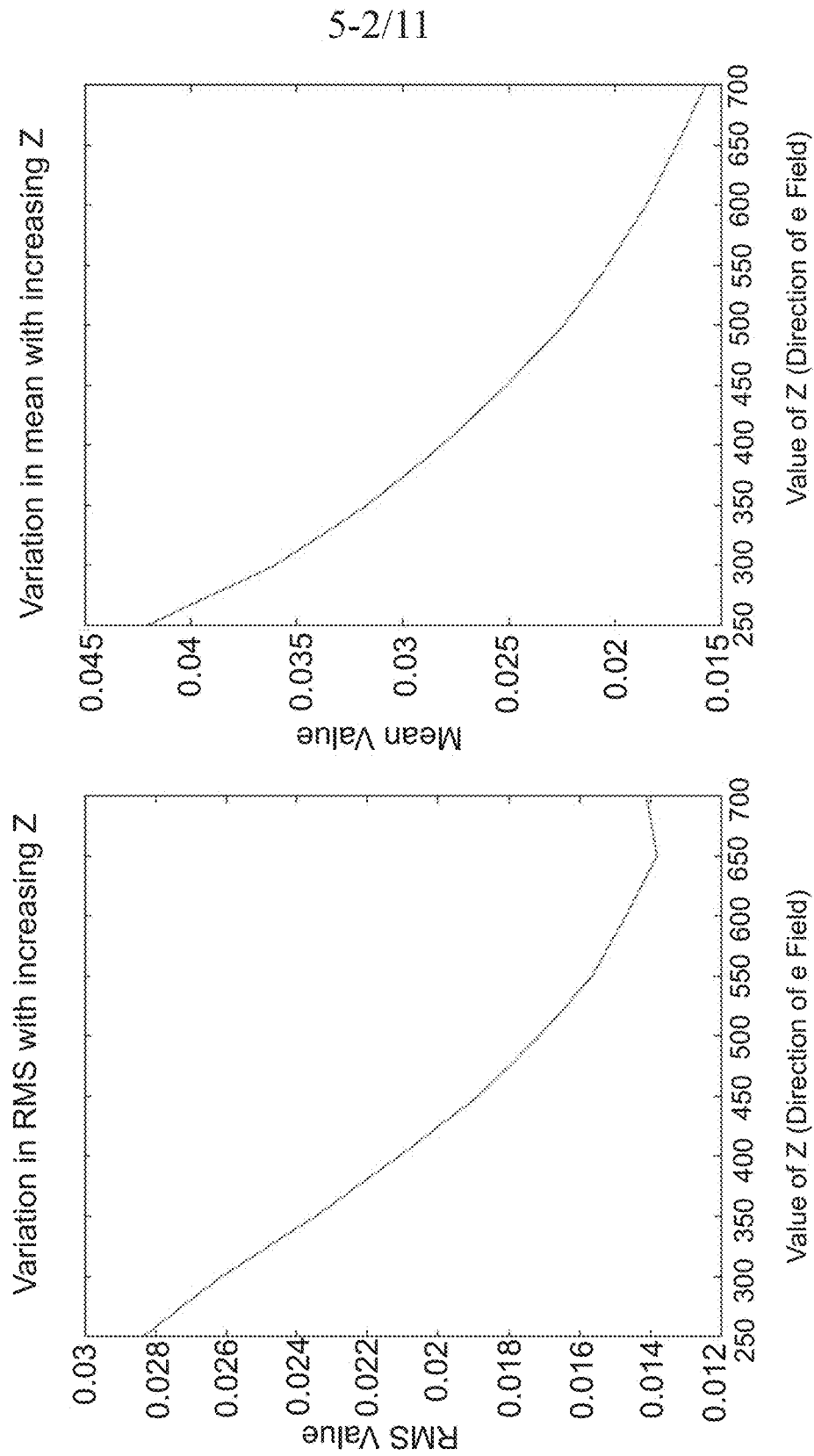
FIG. 6 illustrates an example using EFIRT for 3D reconstructions according to an embodiment of the present invention.

In executing the EFIRT procedure for 3D reconstructions, as the volume of each successive reconstruction increases, the ROI has decreasing information content. As a result, the root mean square (RMS) deviation and mean value of the averaged reconstruction is supposed to be less for each successive reconstruction. This is demonstrated in FIG. 6 showing two graphs: one graph shows the value of the RMS decreasing with respect to the value of z, and the other shows mean value decreasing with respect to the size of z.

Figure 7:
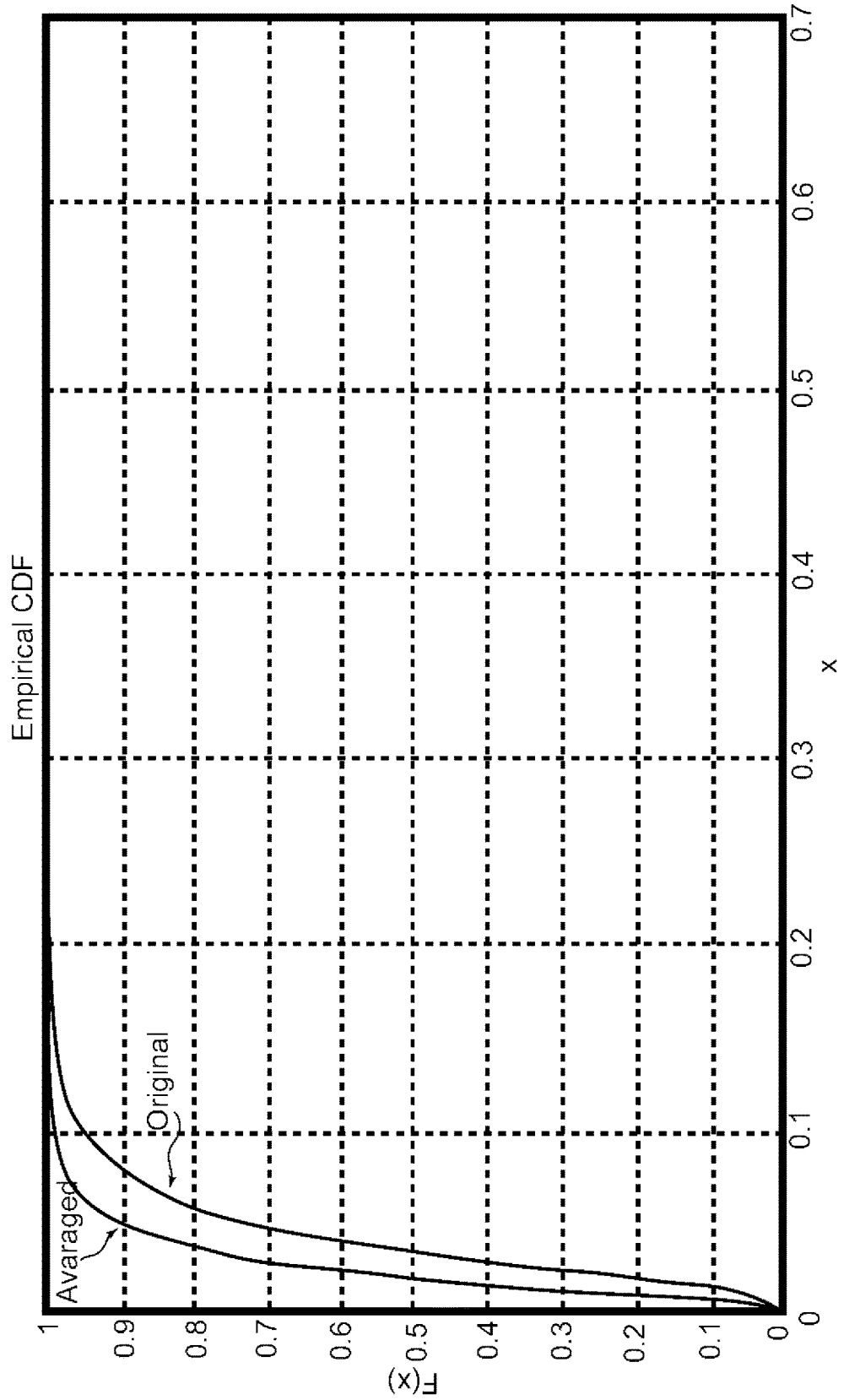
FIG. 7 illustrates an example using EFIRT for 3D reconstructions according to an embodiment of the present invention.

FIG. 7 shows the cumulative density functions (CDF) of the original and the averaged reconstructions. As seen in FIG. 7, the CDF of the averaged reconstruction, i.e., the first curve, goes up faster than the CDF of the original reconstruction, i.e., the second curve. This also shows that the averaged reconstruction has reduced noise.

Figure 8:
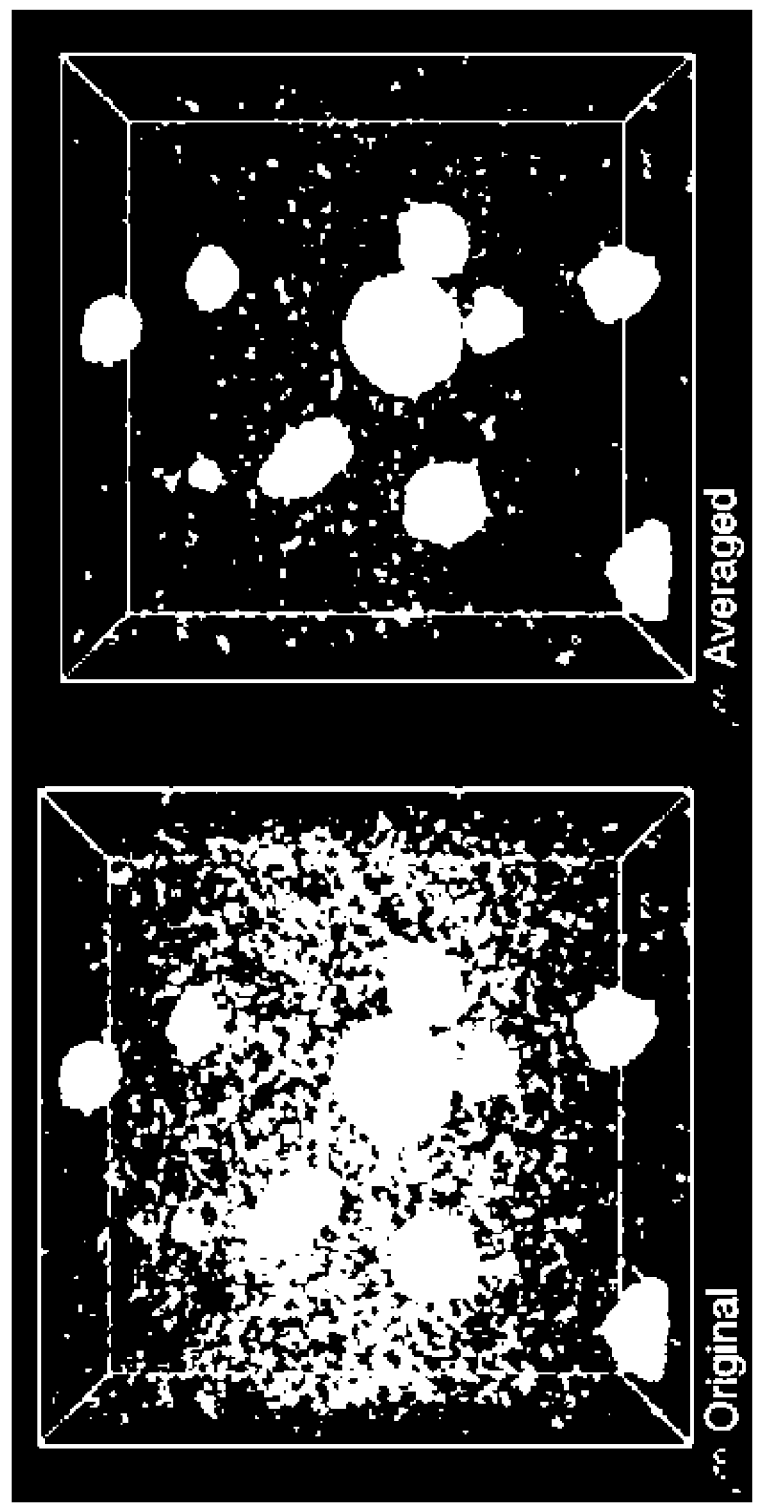
FIG. 8 illustrates another example using EFIRT for 3D reconstructions according to an embodiment of the present invention.
Figure 9:
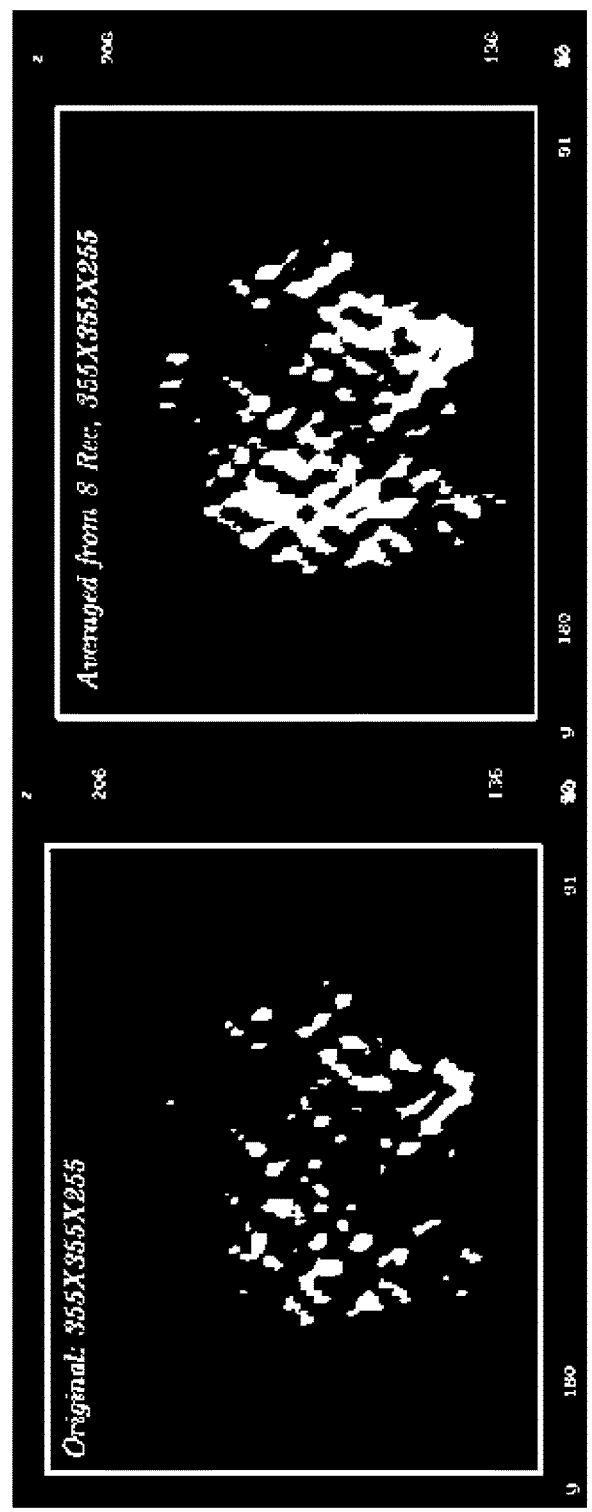
FIG. 9 illustrates another example using EFIRT for 3D reconstructions according to an embodiment of the present invention.
Figure 10:
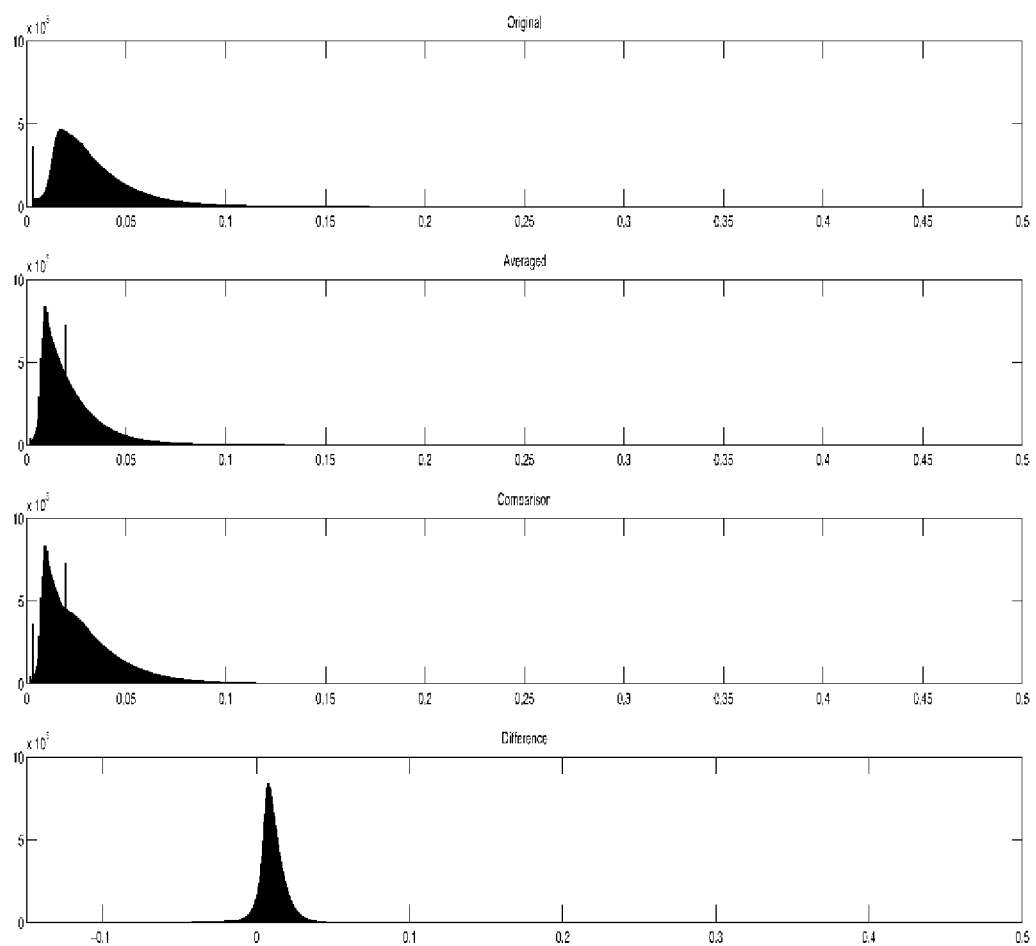
FIG. 10 illustrates another example using EFIRT for 3D reconstructions according to an embodiment of the present invention.

FIGS. 8-10 illustrate another example using EFIRT for 3D reconstructions according to an embodiment of the present invention. In this example, EFIRT is tested for a non-biological sample, which usually does not experience degradation due to electron exposure during imaging. Eight reconstructions were performed starting with 355×355×255 to 355×355×605 with an increment in z of 50 grid points, and on electron micrographs of $SiO_2$ nano particles. The common region 355×355×255 was cut out and averaged from all reconstructions.

FIG. 8 shows the 3D reconstructions of the non-biological sample before and after applying EFIRT. As seen in FIG. 8, the EFIRT-applied reconstruction presents a higher quality than the original reconstruction. The effect of EFIRT is even more obvious in this example because it is not degraded quickly during the TEM imaging, unlike the previous example using a biological sample.

The effect of EFIRT is further visualized in FIG. 9, where thin slices of the 3D reconstructions of a single SiO2 nano particle are shown. Compared to the original reconstruction, the EFIRT-applied and averaged reconstruction shows more information and a higher SNR.

Furthermore, FIG. 10 shows the histograms of the original reconstruction and the averaged reconstruction and their comparison and difference. As shown in the comparison histogram, it is clear that the averaged histogram has lower values than the original histogram, thus having a shift towards the left and a higher peak. Again, the difference histogram shows the amount of noise being removed.

Figure 11:
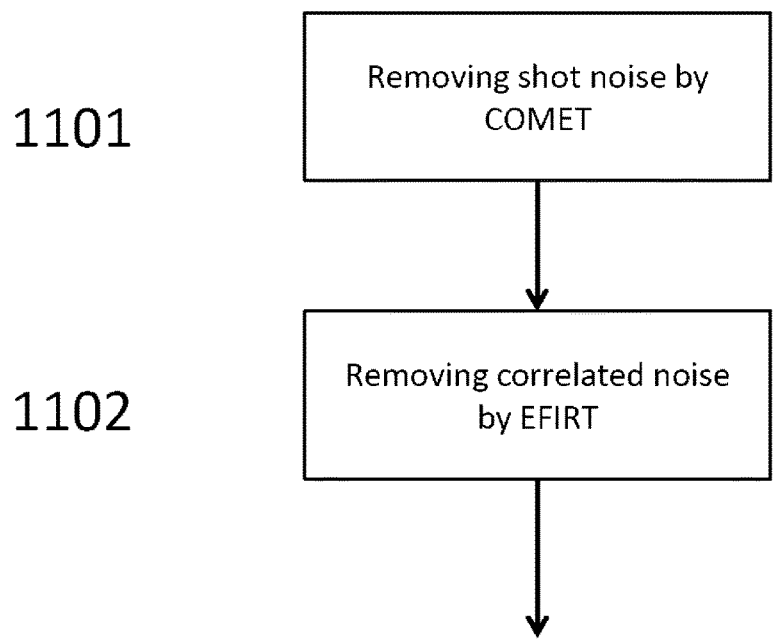
FIG. 11 illustrates an algorithm for improving 3D reconstruction performance by removing uncorrelated and correlated noises according to an embodiment of the present invention.

FIG. 11 illustrates an algorithm for improved 3D reconstruction images by removing uncorrelated and correlated noises according to an embodiment of the present invention. In brief terms, the algorithm in FIG. 11 comprises two steps: Step 1101, removing shot noise or uncorrelated noise with COMET (constrained maximum relative entropy tomography); and Step 1102, removing correlated noise by applying the EFIRT procedure in 3D reconstructions. In one embodiment, as described above, in Step 1102, the EFIRT is applied by performing a set of reconstructions on an extended field larger than the region of interest (ROI), followed by extracting and averaging the ROI from the set of reconstructions. As the set of reconstructions is performed, the volume of each successive reconstruction is increased by increasing z (direction of the electron field).

It should be noted that in some embodiments, the removal of shot noise or uncorrelated noise prior to applying EFIRT to remove correlated noise can be accomplished in various ways, including, without limitation to, COMET. In other embodiments, if the given data set does not contain significant shot noise, then it won't be necessary to remove the shot noise before executing EFIRT to remove correlated noise. In other words, executing EFIRT to remove correlated noise can be a procedure independent of the removal of uncorrelated noise. Also, it should be understood that such algorithm can be applied in various applications including, without limitation to, Cryo-Electron Tomography (Cryo-ET) and other 3D reconstruction procedures/apparatus.

Figure 12:
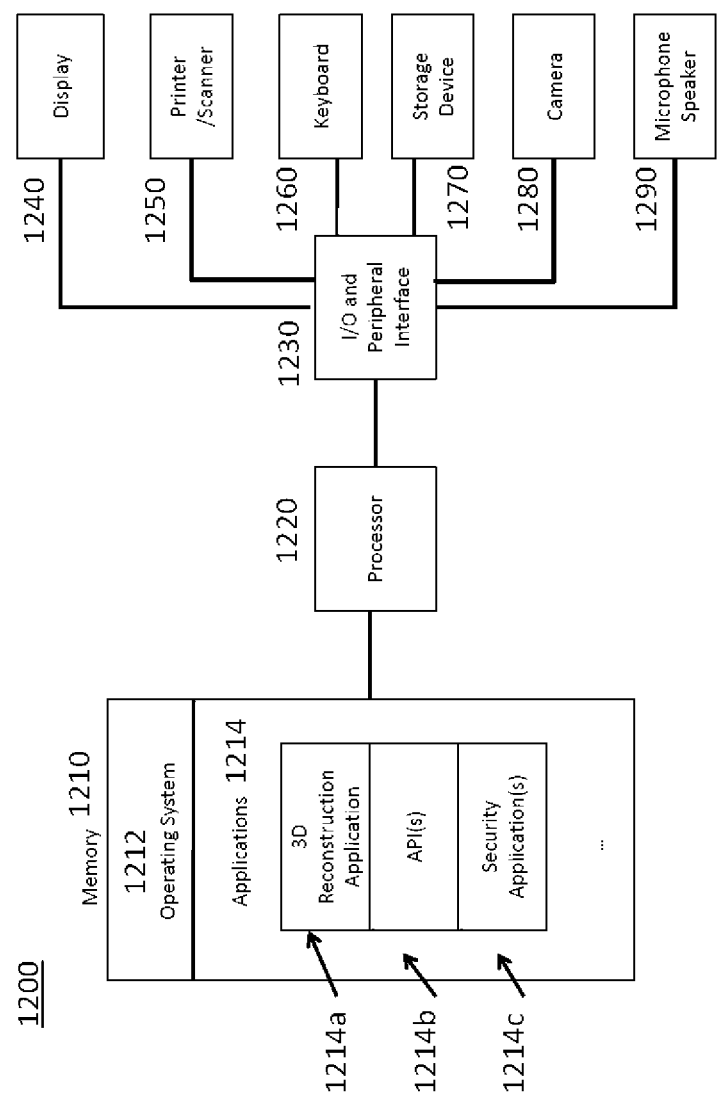
FIG. 12 is a diagram illustrating a computer or data processor for implementing the algorithm of FIG. 11 according to an embodiment of the present invention.

Notably, the algorithm in FIG. 11 can be implemented in data processing software, or a data processor or computer installed with said data processing software. FIG. 12 is a simplified diagram illustrating a computer or data processor for implementing the algorithm of FIG. 11 according to an embodiment of the present invention. It should be noted that the computer 1200 is for illustration only, and many computer components included therein may not be shown or described in the following paragraphs.

As shown in FIG. 12, the computer 1200 comprises a memory 1210, a processor 1220 capable of accessing the memory 1210, and one or more I/O interfaces or other peripheral interfaces 1230 coupled to the processor 1220. Exemplary external or peripheral devices include, without limitation, a display 1240, a keyboard 1260, a camera 1280, a printer or scanner in a combined or separate form 1250, a storage device 1270 such as a USB or disk, and a microphone or speaker 1290. The memory 1210 includes software programs or drivers for activating and communicating with each peripheral device. In one configuration, these components are connected through one or more communication buses (not shown) in the computer, which may include circuitry that interconnects and controls communications between different components.

The memory 1210 includes high-speed random access memory, such as DRAM, SRAM, DDR RAM and/or other random access solid state memory devices; and includes non-volatile memory, such as flash memory devices, a magnetic disk storage device, and/or other non-volatile solid state storage devices. The memory 1210, or alternately non-volatile memory device(s) within the memory 1210, includes a non-transitory computer-readable storage medium. While the memory 1210 is shown as being separate from the processor 1220, all or a portion of the memory 1210 may be embedded in the processor 1220. In some embodiments, the memory 1210 stores the following programs, modules and data structures, or a subset thereof: an operating system 1212 that includes procedures for handling various basic system services and for performing hardware dependent tasks, and applications 1214, including 3D reconstruction application 1214*a* and corresponding APIs 1214*b* for processing data received from other devices and data to be transmitted to the other devices, security applications 1214*c*, and any other applications. In some embodiments, the non-transitory computer-readable storage medium of the memory 1210 includes instructions for performing all or a portion of the operations as described herein. The processor 1220 is configured to access and execute the instructions, programs, applications, and modules stored in the memory 1210.

It will be apparent to those skilled in the art that various modification and variations can be made in the present invention without departing from the spirit or scope of the invention. Thus, it is intended that the present invention cover modifications and variations that come within the scope of the appended claims and their equivalents. In particular, it is explicitly contemplated that any part or whole of any two or more of the embodiments and their modifications described above can be combined and regarded within the scope of the present invention.

REFERENCE SIGNS LIST

1200 Computer or Data Processor
1210 Memory
1220 Processor
1230 I/O interfaces or other peripheral interfaces 1240 Display
1250 Printer/scanner
1260 Keyboard
1270 Storage device
1280 Camera
1290 Microphone/speaker

The invention claimed is:

1. A computer implemented method for removing correlated noise by applying Extended Field Iterative Reconstruction Technique (EFIRT) in a three-dimensional (3D) tomographic reconstruction, said method comprising:
performing a set of successive tomographic reconstructions on an extended field larger than a region of interest (ROI); and
extracting and averaging the ROI from said set of successive tomographic reconstructions,
wherein the set of successive tomographic reconstructions is performed by increasing a volume of the extended field for each successive tomographic reconstruction.

2. The computer implemented method according to claim 1, wherein the volume of the extended field for each successive tomographic reconstruction is increased by increasing one of dimensions defining the volume along a prescribed direction.

3. The computer implemented method according to claim 1, further comprising removing uncorrelated noise in said 3D tomographic reconstruction.

4. The computer implemented method according to claim 1, wherein the 3D tomographic reconstruction is implemented via a Cryo-Electron Tomography (Cryo-ET) application.

5. The computer implemented method according to claim 1,
wherein the 3D tomographic reconstruction is applied to a biological sample.

6. A system for removing correlated noise in a three-dimensional (3D) tomographic reconstruction by applying Extended Field Iterative Reconstruction Technique (EFIRT), said system comprising:
a processor; and
a memory accessible to said processor, wherein said processor is programmed to execute executable instructions stored in said memory, said executable instructions, while executed, causing said processor to:
perform a set of successive tomographic reconstructions on an extended field larger than a region of interest (ROI); and
extract and average the ROI from said set of successive tomographic reconstructions,
wherein said executable instructions, while executed, further causing said processor to perform the set of tomographic reconstructions by increasing a volumes of the extended field for each successive tomographic reconstruction.

7. The system according to claim 6, wherein the volume of the extended field for each successive tomographic reconstruction is increased by increasing one of dimensions defining the volume along a prescribed direction.

8. The system according to claim 6, wherein said executable instructions, while executed, further causing said processor to remove uncorrelated noise in said 3D tomographic reconstruction with COMET or other regularization techniques.

9. The system according to claim 6, wherein the 3D tomographic reconstruction is implemented via a Cryo-Electron Tomography (Cryo-ET) application.

10. The system according to claim 6, wherein the 3D tomographic reconstruction is applied to a biological sample.

* * * * *